(12) United States Patent
Fenster et al.

(10) Patent No.: US 7,297,956 B2
(45) Date of Patent: Nov. 20, 2007

(54) METHODS AND APPARATUS FOR SMALL FOOTPRINT IMAGING SYSTEM

(75) Inventors: Paul Fenster, Petach Tikva (IL); Dov Kariv, Kfar Vradim (IL)

(73) Assignee: General Electric Company, Schenectady, NY (US)

( * ) Notice: Subject to any disclaimer, the term of this patent is extended or adjusted under 35 U.S.C. 154(b) by 232 days.

(21) Appl. No.: 11/189,453

(22) Filed: Jul. 26, 2005

(65) Prior Publication Data

US 2007/0025522 A1    Feb. 1, 2007

(51) Int. Cl.
*G01T 1/16*    (2006.01)
(52) U.S. Cl. .................................. 250/363.08
(58) Field of Classification Search ............... 378/189, 378/197, 198; 250/363.08, 363.05
See application file for complete search history.

(56) References Cited

U.S. PATENT DOCUMENTS

| | | | |
|---|---|---|---|
| 4,209,706 A * | 6/1980 | Nunan ........................ 378/189 |
| 4,426,578 A * | 1/1984 | Bradcovich et al. ... 250/363.08 |
| 5,577,094 A * | 11/1996 | Fudamoto .................... 378/197 |
| 6,147,352 A | 11/2000 | Ashburn | |
| 6,160,258 A | 12/2000 | Maor | |
| 6,180,943 B1 * | 1/2001 | Lange .................... 250/363.05 |

* cited by examiner

*Primary Examiner*—Constantine Hannaher
(74) *Attorney, Agent, or Firm*—Dean D. Small; Small Patent Law Group

(57) ABSTRACT

A method and system for imaging a patient is provided. The system includes an arcuate detector transport member that extends circumferentially about an examination axis, a base comprising an arcuate transport element configured to receive the detector transport member wherein the base is configured to translate the arcuate detector transport member in an arcuate path about the examination axis, and at least one gamma camera detector coupled to the detector transport member.

31 Claims, 3 Drawing Sheets

METHODS AND APPARATUS FOR SMALL FOOTPRINT IMAGING SYSTEM

BACKGROUND OF THE INVENTION

This invention relates generally to imaging systems, and more particularly to a movable imaging system detector support apparatus.

Imaging devices, such as gamma cameras and computed tomography (CT) imaging systems, are used in the medical field to detect radioactive emission events emanating from an object, and to detect transmission x-rays or transmission gamma rays attenuated by the object, respectively. An output, typically in the form of an image that graphically illustrates the distribution of the emissions within the object and/or the distribution of attenuation of the object is formed from these detections. An imaging device may have one or more detectors that detect the number of emissions, for example, gamma rays in the range of about seventy keV to about six hundred keV, and may have one or more detectors to detect x-rays and/or gamma rays that have passed through the object.

Some known imaging systems include a closed ring gantry. To image a patient using a closed ring gantry, the patient ingresses and egresses the viewing area using a long travel bed that moves the patient longitudinally along an examination axis. However, such an ingress/egress configuration requires additional examining room floor space. This additional floor space is not usable during an imaging scan, but must be available during a scan to allow egress of the patient at the completion of the scan. A closed-ring gantry is also known to be less comfortable for the patient due to the claustrophobically close clearances of the gantry to the patient.

U.S. Pat. No. 6,147,352 describes a gamma camera comprising a gamma camera head. The head is enclosed within a stationary carrier which extends more than 180 degrees (but less than 360°) around the patient. The gamma camera head moves along rails within the carrier to provide nuclear medicine images having views over 180° around the patient.

Nucline™ Cardio-C marketed by Medisco Medical Imaging Systems of Budapest, Hungary, is a dual head gamma camera in which the heads are enclosed within a stationary carrier. The dual heads rotate at least 90° about the patent along rails within the stationary carrier to provide views over a range of 180°.

BRIEF DESCRIPTION OF THE INVENTION

In one embodiment, a medical imaging system is provided. The medical imaging system includes an arcuate detector transport member that extends circumferentially about an examination axis, a base including an arcuate transport element configured to receive the detector transport member such that the detector transport member is supported by a rolling member wherein the base is configured to translate the arcuate detector transport member along the rolling member in an arcuate path about the examination axis, and at least one gamma camera detector coupled to the detector transport member.

In another embodiment, a method of imaging a patient is provided. The method includes coupling at least one detector to a detector transport member, the at least one detector configured to move with the detector transport member, the detector transport member spanning an arc of less than about one hundred eighty degrees about an examination axis, supporting the detector transport member with a base having a support assembly that includes rolling elements wherein the support assembly is configured to engage the detector transport member, and rotating the detector transport member on the rolling elements through a predetermined path about the examination axis to a plurality of imaging positions.

In yet another embodiment, a method for medical imaging is provided. The method includes coupling at least one nuclear medicine detector to a detector transport member, supporting the detector transport member with an arcuate base having an arcuate support assembly configured to receive the detector transport member, the base remaining stationary with respect to an examination axis, and translating the detector transport member along an arcuate path about the examination axis.

DETAILED DESCRIPTION OF THE INVENTION

Figure 1:
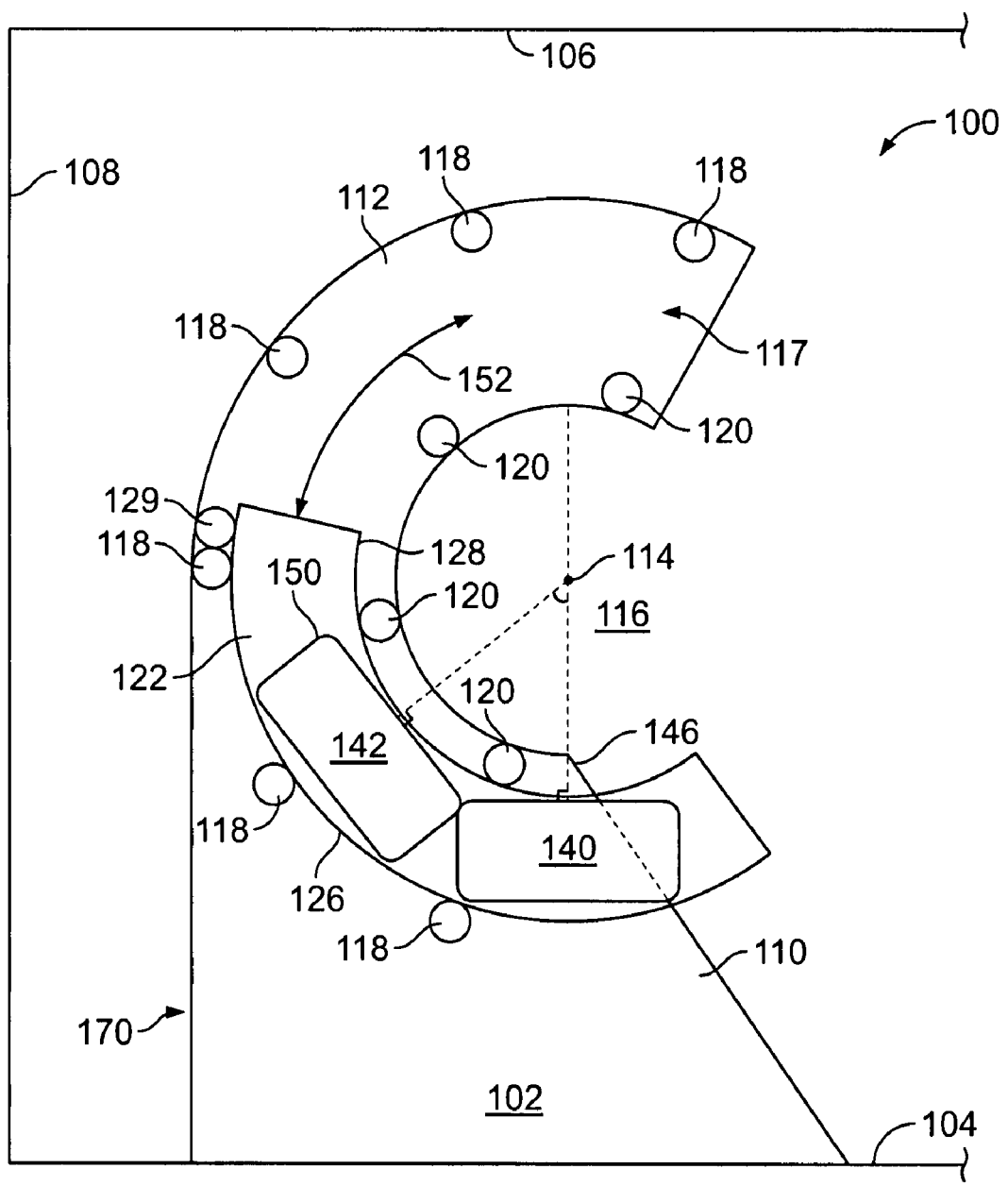
FIG. 1 is a side elevation view of an imaging system in accordance with an exemplary embodiment of the present invention in a first imaging position.

FIG. 1 is a side elevation view of an imaging system 100 in accordance with an exemplary embodiment of the present invention. Imaging system 100 includes a base 102 that may be configured to be fixedly coupled to, for example, a floor surface 104, a ceiling surface 106, and/or a wall surface 108 or by simply resting base 102 on floor surface 104 such that imaging system 100 is balanced and stable. Base 102 may be coupled to floor surface 104, ceiling surface 106, and/or wall surface 108 by, for example, welding, threaded fasteners, and/or clamping fasteners. Imaging system 100 may weigh several thousand pounds. In a configuration wherein imaging system 100 is coupled to ceiling surface 106, and/or wall surface 108, an additional support (not shown) may be used to further support base 102 from floor surface 104. Base 102 includes a support portion 110 and a stator portion 112. In the exemplary embodiment, stator portion 112 is substantially arcuately-shaped about an examination axis 114 of an examination area 116 that is generally circular about examination axis 114. A portion of stator portion 112 is open such that a subject may enter the examination area 116 perpendicularly to examination axis 114. A transport base structure 117 may be coupled to stator portion 112 to provide an arcuate path of motion for a detector transport member 122, in a direction 152 that partially circumscribes examination area 116. In the exemplary embodiment, transport element is defined by a plurality of rolling members, such as, radially outer leading wheels 118 and radially inner leading wheels 120 that are rotatably coupled to stator portion 112 in two substantially concentric arcs about examination axis 114.

Detector transport member 122 includes an arcuately-shaped body having guide members, such as a radially outer peripheral edge 126 and a radially inner peripheral edge 128. Transport base element 117 is configured to engage detector transport member 122 to permit detector transport member 122 to move in an arcuate path about examination area 116. In the exemplary embodiment, wheels 118 and 120 may engage outer peripheral edge 126 and inner peripheral edge 128 in rolling engagement. In an alternative embodiment, a guide member, such as an interior edge (not shown) is formed along detector transport member 122 between outer peripheral edge 126 and inner peripheral edge 128 and wheels 118 and 120 engage the interior edge. A detector transport drive 129 includes a prime mover, such as a motor and a means to transfer rotational power from the motor to detector transport member 122. In one embodiment, detector transport drive 129 includes a motor mounted to stator 112. The motor includes a pinion (not shown) coupled to the motor shaft and detector transport drive 129 also includes a rack (not shown) coupled to detector transport member 122. In combination, the pinion and rack transfer rotational power from the motor to detector transport member 122 to drive detector transport member 122 through an arcuate path about examination area 116 during a scan. In other various embodiments, detector transport drive 129 includes other drive components, such as a belt and sheave arrangement or a chain and sprocket drive.

In the exemplary embodiment, two gamma camera radiation detectors 140 and 142 each optionally having a substantially rectangular polyhedrally shaped body are mounted on or otherwise coupled to detector transport member 122. An edge 144 of a detecting face 146 of gamma camera radiation detector 140 is optionally arranged to be proximate an edge 148 of a detecting face 150 of gamma camera radiation detector 142 wherein detecting faces 146 and 150 are oriented substantially perpendicular with respect to each other. In an alternative embodiment, gamma camera radiation detectors 140 and 142 may be oriented in an angle other than ninety degrees with respect to each other. In another alternative embodiment, only one of gamma camera radiation detectors 140 and 142 is used such that imaging system 100 only includes a single gamma camera radiation detector 140. Generally, either or both of gamma camera radiation detectors 140 and 142 are oriented such that a normal centerline of a face of the at least one detector is oriented substantially orthogonally to examination axis 114, but gamma camera radiation detector 140 may be oriented at other angles with respect to examination axis 114.

In the exemplary embodiment, both of detectors 140 and 142 are used for emission imaging. Detector 142 and/or detector 140 may be simultaneously used for transmission imaging with a source (not shown), for example, but not limited to a transmission x-ray source and/or a transmission gamma source positioned opposite the detector, providing x-ray photons and/or transmission gamma rays at an energy level that may be different than the emission gamma energy levels. The detector collects both emission gammas and transmission x-ray photons and/or transmission gamma rays, identifies the different photon energy levels and generates transmission data simultaneously. The two detector arrangement allows performing a scan of about one hundred eighty degrees about examination axis 114 while moving detectors 140 and 142 only through about ninety degrees of rotation about examination axis 114. The two detector arrangement also allows performing a scan of a region of a patient from two view angles simultaneously.

Detector transport member 122 is configured to translate gamma camera radiation detectors 140 and 142 along arcuate path 152 at least partially circumscribing examination axis 114. Detectors 140 and 142 may include a tilting base (not shown) configured to modify the alignment of detectors 140 and 142 with respect to examination axis 114. Detectors 140 and 142 may be coupled to detector transport member 122 such that detectors 140 and 142 move along an arcuate path with detector transport member 122 and do not substantially move along the arcuate path with respect to detector transport member 122. Detectors 140 and 142 may include radiation detectors constructed from, for example, scintillation materials such as sodium iodide or cesium iodide with associated photomultiplier tubes or other photodetectors such as solid state photodiodes, radiation-sensitive scintillation material and a light detecting device, or may be fabricated from a semiconductor radiation detector including, for example, but not limited to, cadmium zinc telluride (CZT).

In a first position 170, shown in FIG. 1, detector transport member 122 may be positioned such that detector 140 is located beneath examination axis 114 and detector 142 is located in an adjacent position.

Figure 2:
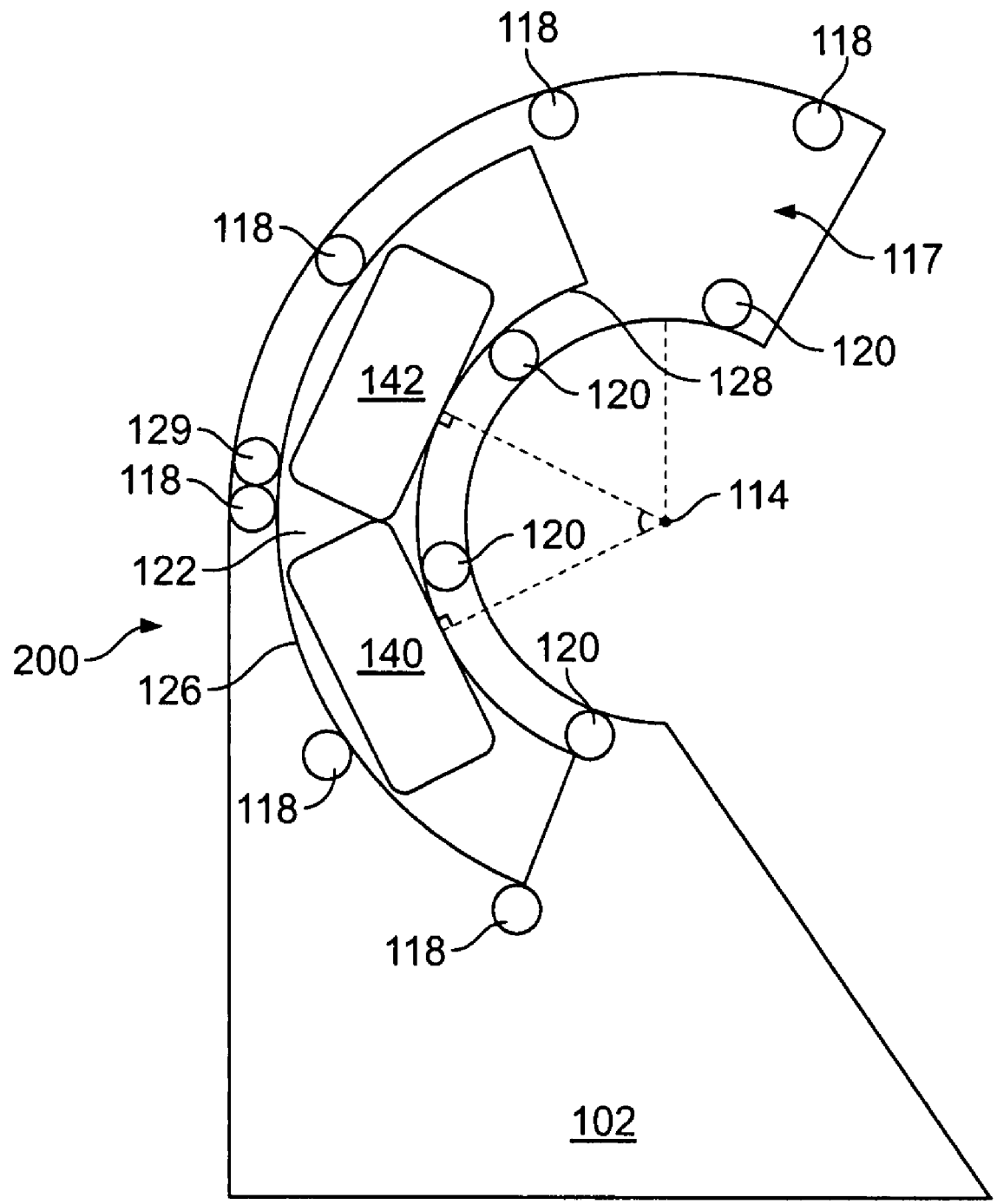
FIG. 2 is a side elevation view of the imaging system shown in FIG. 1 in an exemplary second imaging position.

FIG. 2 is a side elevation view of imaging system 100 in accordance with an exemplary embodiment of the present invention. In a second position 200, detector transport member 122 may be positioned such that detector 140 and detector 142 are both located on the side of examination axis 114.

Figure 3:
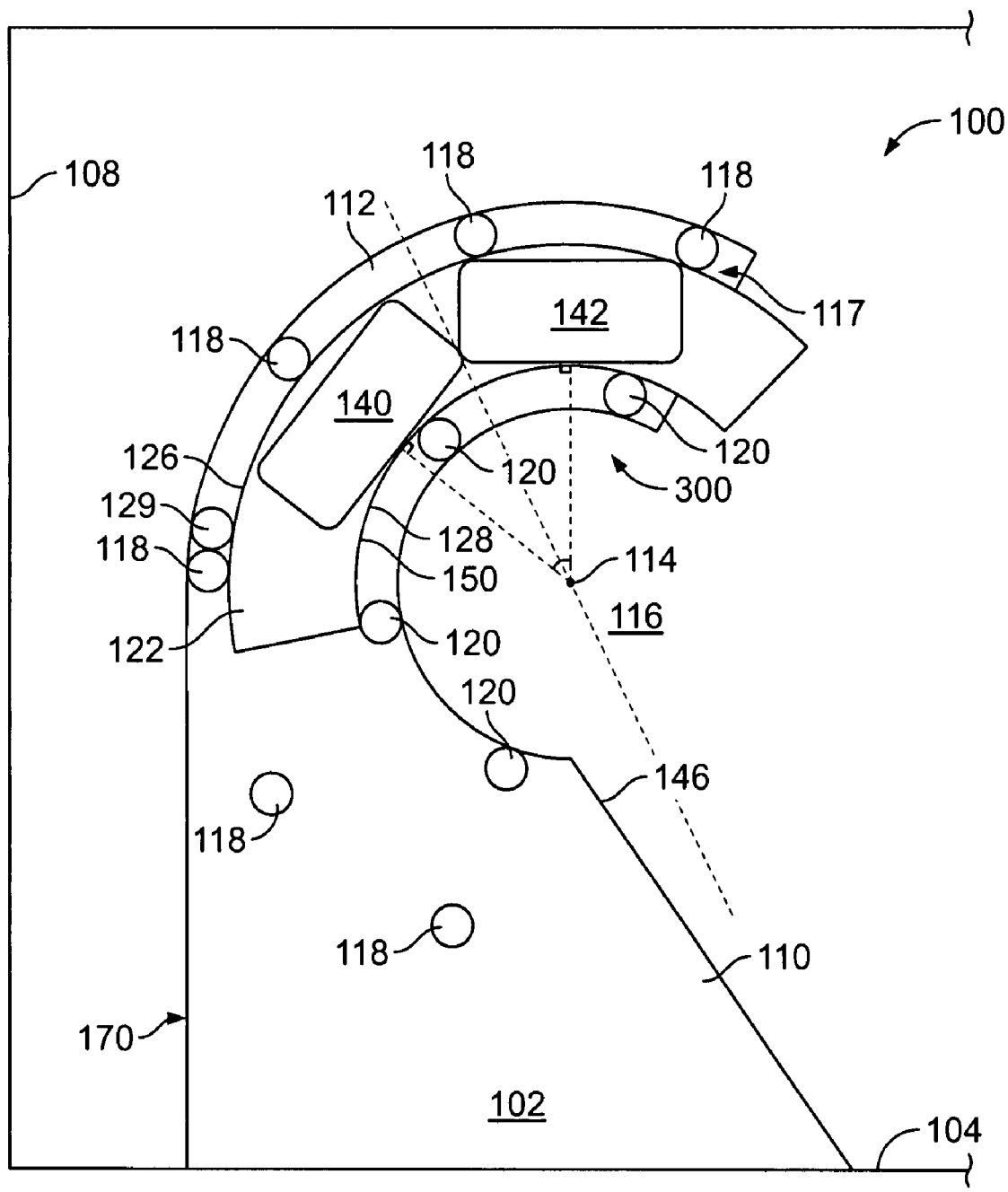
FIG. 3 is a side elevation view of the imaging system shown in FIG. 1 in an exemplary third imaging position.

FIG. 3 is a side elevation view of imaging system 100 in accordance with an exemplary embodiment of the present invention. In a third position 300, detector transport member 122 may be positioned such that detector 142 is located in a position opposite that of detector 140 in FIG. 1. In an alternative embodiment, because, in the position shown, detector 142 provides information similar to that provided by detector 140 in FIG. 1, the final position of detectors 140 and 142 is counter-clockwise to the position shown in FIG. 1.

In operation, detector transport member 122 begins a scan in a first position 170. Detector transport drive 129 may be controlled to rotate in a direction that causes detector transport member 122 to move along arcuate path 152 from position 170 to position 300 or any intermediate position therebetween. If a tomographic image (such as a SPECT image) is desired, the detector optionally pauses at increments along the path and acquires emission data from a patient. Alternatively, imaging may start at any other position and progress in any direction. A scan may include motion in one or more portions along path 152 in any direction.

The emission data may be acquired at only a single position. This is especially useful when the detectors 140 and 142 are oriented at 90° to each other, for viewing the heart from two directions. The imaging system is also configured to be used for planar imaging or biplane imaging of the heart or other portions of the body.

The acquired data is passed to an imaging computer (not shown) for generation of images from the emission data and their display on a display (not shown) as is well known in the art.

The above-described embodiments of an imaging system provide a cost-effective and reliable means for examining a patient. More specifically, the imaging system includes a relatively small floor space requirement by using an open gantry that allows patient ingress to and egress from an imaging system 100 viewing area through a gap in the gantry. A detector transport member 122 of the imaging system 100 is moved away from a patient's ingress path by retracting the detector support member 122 in telescoping fashion adjacent to an imaging system base 102.

Exemplary embodiments of imaging system methods and apparatus are described above in detail. The imaging system components illustrated are not limited to the specific embodiments described herein, but rather, components of each imaging system may be utilized independently and separately from other components described herein. For example, the imaging system components described above may also be used in combination with different imaging systems. A technical effect of the various embodiments of the systems and methods described herein include at least one of facilitating reducing imaging system sitting requirements by reducing a floor space requirement of the imaging system.

While the invention has been described in terms of various specific embodiments, those skilled in the art will recognize that the invention can be practiced with modification within the spirit and scope of the claims.

What is claimed is:

1. A medical imaging system comprising:
    an arcuate detector transport member that extends circumferentially about an examination axis;
    a base comprising an arcuate transport element configured to receive said detector transport member such that said detector transport member is supported by a rolling member, said base configured to translate said arcuate detector transport member along said rolling member in an arcuate path about said examination axis; and
    at least one gamma camera detector coupled to said detector transport member, wherein a face of the detector is oriented orthogonally to said examination axis.

2. A medical imaging system in accordance with claim 1 wherein said detector transport member extends less than about two hundred seventy degrees circumferentially about said examination axis.

3. A medical imaging system in accordance with claim 2 wherein said arcuate detector transport member extends less than about one hundred eighty degrees circumferentially about said examination axis.

4. A medical imaging system in accordance with claim 1 wherein said detector transport member is moveable along an arc defined by said transport element.

5. A medical imaging system in accordance with claim 1 wherein said base further comprises a pinion gear coupled to a motor, said detector transport member further comprises a toothed rack configured to engage said pinion gear, said rack and said pinion configured to transmit a force from said motor to said detector transport member that causes said detector transport member to move relative to said base.

6. A medical imaging system in accordance with claim 5 wherein said pinion gear is powered from an electric motor.

7. A medical imaging system in accordance with claim 6 wherein said electric motor is powered from an electrical source located in said base.

8. A medical imaging system in accordance with claim 1 wherein said detector transport member comprises a guide member configured to engage a plurality of rolling members, said guide member configured to guide said detector transport member along an arcuate path.

9. A medical imaging system in accordance with claim 8 wherein said plurality of rolling members comprises a groove and wherein said guide member comprises an edge, said edge configured to engage said groove.

10. A medical imaging system in accordance with claim 8 wherein said plurality of rolling members comprises an edge and wherein said guide member comprises a groove, said edge configured to engage said groove.

11. A medical imaging system in accordance with claim 1 wherein said base is configured to rotate said arcuate detector transport member about said examination axis through an arc of less than about one hundred eighty degrees.

12. A medical imaging system in accordance with claim 11 wherein said base is configured to rotate said arcuate detector transport member about said examination axis through an arc of about ninety degrees.

13. A medical imaging system in accordance with claim 11 wherein said base is configured to rotate said arcuate detector transport member about said examination axis through an arc of less than about ninety degrees.

14. A medical imaging system in accordance with claim 1 wherein said at least one detector comprises cadmium zinc telluride (CZT).

15. A medical imaging system in accordance with claim 1 wherein said at least one detector is configured to receive emission gamma rays at each of said at least one of a plurality of imaging positions, said emission gamma rays emitted from an imaging volume proximate said examination axis.

16. A medical imaging system in accordance with claim 1 wherein said at least one detector comprises two detectors, each detector oriented at about ninety degrees with respect to the other.

17. A method of imaging a patient comprising:
    coupling at least one detector to a detector transport member, the at least one detector configured to move with the detector transport member, the detector transport member spanning an arc of less than about one hundred eighty degrees about an examination axis, wherein a face of the detector is oriented orthogonally to the examination axis;
    supporting the detector transport member with a base including a support assembly that includes rolling elements, the support assembly configured to engage the detector transport member; and
    rotating the detector transport member on the rolling elements through a predetermined path about the examination axis to a plurality of imaging positions, wherein the at least one detector includes a detecting face having an edge and wherein coupling at least one detector to a detector transport member comprises coupling a pair of radiation detectors together such that the edge of a first of the pair of radiation detectors is proximate and parallel the edge of a second of the pair of radiation detectors.

18. A method of imaging a patient accordance with claim 17 wherein coupling a pair of radiation detectors together comprises coupling the detectors such that the detecting faces are oriented substantially perpendicular with respect to each other.

19. A method of imaging a patient in accordance with claim 17 wherein coupling at least one detector to a detector transport member comprises coupling at least one gamma camera to the detector transport member.

20. A method of imaging a patient in accordance with claim 17 wherein coupling at least one detector to a detector transport member comprises coupling the at least one detector to the detector transport member such that a normal centerline of a face of the at least one detector is oriented substantially orthogonally to the examination axis.

21. A method of imaging a patient in accordance with claim 17 further comprising positioning a patient through a gap in the detector transport member where the patient is substantially aligned with the examination axis.

22. A method of imaging a patient in accordance with claim 17 wherein the detector transport member includes a rack and the base includes a complementary pinion and wherein rotating the detector transport member about the examination axis comprises controlling the rotation of an electrical motor coupled to the pinion to at least one of move the detector transport member between a plurality of imaging positions and maintain the detector transport member substantially stationary at an imaging position.

23. A method of imaging a patient in accordance with claim 22 further comprising powering the motor from an electrical source located in the base.

24. A method of imaging a patient in accordance with claim 17 wherein rotating the detector transport member about the examination axis comprises rotating the detector transport member less than about one hundred eighty degrees while imaging the patient.

25. A method of imaging a patient in accordance with claim 24 wherein rotating the detector transport member about the examination axis comprises rotating the detector transport member about ninety degrees while imaging the patient.

26. A method of imaging a patient in accordance with claim 24 wherein rotating the detector transport member about the examination axis comprises rotating the detector transport member about ninety degrees while receiving images corresponding to an about one hundred eighty degree scan of the patient.

27. A method of imaging a patient in accordance with claim 17 further comprising receiving at least one of transmission x-ray photons, transmission gamma rays, and emission gamma rays using the at least one detector.

28. A method for medical imaging comprising:
coupling at least one nuclear medicine detector to a detector transport member;
supporting the detector transport member with an arcuate base having an arcuate support assembly that includes rolling elements configured to receive the detector transport member, the base remaining stationary with respect to an examination axis; and
translating the detector transport member, using the rolling elements, along an arcuate path about the examination axis, wherein a face of the detector is oriented orthogonally to the examination axis.

29. A method for medical imaging in accordance with claim 28 further comprising coupling a pair of nuclear medicine detectors to the detector transport member such that an edge of a detecting face of a first of the pair of nuclear medicine detectors is proximate an edge of a detecting face of a second of the pair of nuclear medicine detectors wherein the detecting faces are oriented substantially perpendicular with respect to each other.

30. A method for medical imaging in accordance with claim 28 wherein said rotating a detector transport member comprises at least one of rotating the detector transport member intermittently between a plurality of imaging positions and rotating the detector transport member continuously from a imaging start position to a imaging finish position.

31. A method for medical imaging in accordance with claim 30 wherein said rotating a detector transport member comprises rotating the detector transport member through an arc of less than about one hundred eighty degrees about the examination axis from the imaging start position to the imaging finish position.

* * * * *